US010124101B2

(12) United States Patent
Wong et al.

(10) Patent No.: US 10,124,101 B2
(45) Date of Patent: Nov. 13, 2018

(54) FLUID RESISTANT LOCKING ELECTRICAL CONNECTOR FOR VENTRICULAR ASSIST DEVICES

(71) Applicant: TC1 LLC, St. Paul, MN (US)

(72) Inventors: Kenneth Wong, Saratoga, CA (US); George Chao-chih Hsu, San Ramon, CA (US); Thomas Orduna, Oakley, CA (US); Shahn S. Sage, Andover, MN (US)

(73) Assignee: TC1 LLC, St. Paul, MN (US)

( * ) Notice: Subject to any disclaimer, the term of this patent is extended or adjusted under 35 U.S.C. 154(b) by 0 days.

(21) Appl. No.: 15/659,366

(22) Filed: Jul. 25, 2017

(65) Prior Publication Data

US 2018/0028736 A1 Feb. 1, 2018

Related U.S. Application Data

(60) Provisional application No. 62/367,566, filed on Jul. 27, 2016.

(51) Int. Cl.
*A61M 1/12* (2006.01)
*H01R 31/02* (2006.01)
*A61M 1/10* (2006.01)
*A61M 39/10* (2006.01)
*H01R 105/00* (2006.01)
*H01R 13/639* (2006.01)
(Continued)

(52) U.S. Cl.
CPC .............. *A61M 1/122* (2014.02); *A61M 1/10* (2013.01); *A61M 1/101* (2013.01); *A61M 1/127* (2013.01); *H01R 31/02* (2013.01); *A61M 5/14276* (2013.01); *A61M 2039/1077* (2013.01); *H01R 13/639* (2013.01); *H01R 24/28* (2013.01); *H01R 2105/00* (2013.01); *H01R 2201/12* (2013.01)

(58) Field of Classification Search
CPC ............................... A61M 1/122; H01R 31/02
USPC ......................................................... 439/180
See application file for complete search history.

(56) References Cited

U.S. PATENT DOCUMENTS

| 4,010,998 A * | 3/1977 | Tolnar, Jr. | H01R 13/6273 439/358 |
| 4,148,538 A * | 4/1979 | Rodondi | H01R 13/6278 439/347 |

(Continued)

*Primary Examiner* — Alexander Gilman
(74) *Attorney, Agent, or Firm* — Kilpatrick, Townsend & Stockton LLP (57) ABSTRACT

A fluid resistant electrical connector for an implantable medical device includes a first connector assembly and a second connector assembly. The first connector assembly includes a first housing, an elongated coupling member, and first electrical contacts distributed around the coupling member. The second connector assembly includes a second housing, second electrical contacts, and a retention member. The second housing has a coupling member receptacle and a retention member receptacle. The coupling member receptacle is shaped to accommodate a distal portion of the coupling member. The retention member is partially accommodated by the retention member receptacle and movable between an insertion configuration accommodating coupling of the first and second connector assemblies and a retention configuration retaining the coupling member to prevent inadvertent uncoupling of the electrical connector.

23 Claims, 7 Drawing Sheets

(51) Int. Cl.
*H01R 24/28* (2011.01)
*A61M 5/142* (2006.01)

(56) References Cited

U.S. PATENT DOCUMENTS

| | | | | |
|---|---|---|---|---|
| 4,561,682 A * | 12/1985 | Tisserat | ................ | F16L 37/144 |
| | | | | 285/305 |
| 4,810,241 A * | 3/1989 | Rogers | ................ | A61M 39/16 |
| | | | | 604/28 |
| 5,016,922 A * | 5/1991 | Le Mer | ................ | F16L 37/144 |
| | | | | 285/305 |
| 5,429,616 A * | 7/1995 | Schaffer | ............ | A61M 25/0606 |
| | | | | 604/167.06 |
| 5,749,859 A * | 5/1998 | Powell | ............. | A61M 25/0637 |
| | | | | 604/167.03 |
| 6,332,800 B2 * | 12/2001 | Kodama | ............ | H01R 13/6273 |
| | | | | 439/357 |
| 6,520,546 B2 * | 2/2003 | Szabo | ................... | F16L 37/144 |
| | | | | 285/308 |
| 7,344,527 B2 * | 3/2008 | Schweikert | ........... | A61M 39/10 |
| | | | | 604/250 |
| 7,390,210 B2 * | 6/2008 | Corona | ............ | B29C 45/14065 |
| | | | | 439/281 |
| 7,678,101 B2 * | 3/2010 | Sage | ................... | A61M 39/1011 |
| | | | | 604/533 |
| 7,794,288 B2 * | 9/2010 | Shindo | ................. | H01R 13/533 |
| | | | | 439/347 |
| 7,862,366 B2 * | 1/2011 | Stone | ................. | H01R 13/5219 |
| | | | | 285/305 |
| 7,972,167 B2 * | 7/2011 | Amit | .................... | B60L 11/005 |
| | | | | 439/456 |
| 9,142,914 B2 * | 9/2015 | Jozwik | ............ | H01R 13/622 |
| 9,153,889 B2 * | 10/2015 | Germ | ..................... | H01R 13/02 |
| 9,334,634 B2 * | 5/2016 | Bares | ................... | E03C 1/0403 |
| 2009/0325416 A1 * | 12/2009 | Shindo | ................. | H01R 13/533 |
| | | | | 439/346 |
| 2014/0339820 A1 * | 11/2014 | Suilmann | ............ | F16L 37/144 |
| | | | | 285/319 |
| 2015/0295341 A1 * | 10/2015 | Elmvang | ............ | H01R 13/642 |
| | | | | 439/374 |

* cited by examiner

FLUID RESISTANT LOCKING ELECTRICAL CONNECTOR FOR VENTRICULAR ASSIST DEVICES

CROSS-REFERENCES TO RELATED APPLICATIONS

This application claims the benefit of U.S. Provisional Application No. 62/367,566, filed Jul. 27, 2016, the entire contents of which are incorporated herein by reference for all purposes.

BACKGROUND

Ventricular assist devices, known as VADs, often include an implantable blood pump and are used for both short-term (i.e., days, months) and long-term applications (i.e., years or a lifetime) where a patient's heart is incapable of providing adequate circulation, a condition commonly referred to as heart failure or congestive heart failure. According to the American Heart Association, more than five million Americans are living with heart failure, with about 670,000 new cases diagnosed every year. People with heart failure often have shortness of breath and fatigue. Years of living with blocked arteries or high blood pressure can leave a heart too weak to pump enough blood to the body. As symptoms worsen, advanced heart failure develops.

A patient suffering from heart failure may use a VAD while awaiting a heart transplant or as a long-term destination therapy. In another example, a patient may use a VAD while recovering from heart surgery. Thus, a VAD can supplement a weak heart (i.e., partial support) or can effectively replace the natural heart's function. In view of the critical nature of the support provided by a mechanical circulatory support (MCS) system, it is essential that power supplied to the MCS system not be interrupted for any significant period of time so as to avoid endangering the life of the patient.

Typically, a VAD is electrically powered. A power cable is often employed to transfer electric power to the implanted pump and/or to an implanted control unit for the VAD. An electrical connector for connecting the power cable to the implanted pump or the implanted control unit can be used to make it easier to implant the pump and/or the control unit. The electrical connector can also make it easier to replace the implanted pump, the control unit, and/or the power cable by providing for disconnection of the power cable.

Existing electrical connectors, however, may not be suitable for implantation. For example, existing electrical connectors may permit detrimental fluid ingression into the connector. There is the continuing need for electrical connectors with improved resistance to corrosion and infection. Also, existing electrical connectors may have latching mechanisms that are not suitable for an implanted environment. Accordingly, electrical connectors suitable of implantation are of interest.

BRIEF SUMMARY

The following presents a simplified summary of some embodiments of the invention in order to provide a basic understanding of the invention. This summary is not an extensive overview of the invention. It is not intended to identify key/critical elements of the invention or to delineate the scope of the invention. Its sole purpose is to present some embodiments of the invention in a simplified form as a prelude to the more detailed description that is presented later.

Electrical connectors are provided that are suitable for use with implanted medical devices. In some embodiments, the electrical connector includes an elongated coupling member that can be engaged by a retention member to prevent unintended decoupling of the electrical connector. In some embodiments, the retention member is movable between a first position accommodating coupling and decoupling of the electrical connector and a second position that blocks decoupling of the electrical connector. In some embodiments, the retention member can be retained in the second position to prevent unintended decoupling of the electrical connector. In some embodiments, the electrical connector includes one or more seals that inhibit fluid ingress into the electrical connector. The electrical connectors described herein are especially suitable for use with implanted medical devices in view of the features that prevent fluid ingress and unintended decoupling, while still accommodating intentional decoupling of the electrical connector.

Thus, in one aspect, a fluid resistant electrical connector suitable for use with an implantable medical device includes a first connector assembly and a second connector assembly configured to be connected with the first connector assembly. The first connector assembly includes a first housing, an elongated coupling member, and first electrical contacts. The coupling member is mounted to the first housing and extends in a direction towards a distal end of the first housing. The first electrical contacts are mounted to the first housing, distributed around the coupling member, and extend in the direction towards the distal end of the first housing. The second connector assembly includes a second housing, second electrical contacts, and a retention member. The second housing has a coupling member receptacle and a retention member receptacle. The coupling member receptacle is shaped to accommodate a distal portion of the coupling member when the second connector assembly is connected with the first connector assembly. The retention member receptacle is oriented transverse to and intersects the coupling member receptacle. The second electrical contacts are mounted to the second housing. Each of the second electrical contacts is configured to couple with a respective one of the first electrical contacts when the second connector assembly is connected with the first connector assembly. The retention member is at least partially accommodated by the retention member receptacle. The retention member is moveable transverse to the direction towards the distal end of the first housing to retain the distal portion of the coupling member in the coupling member receptacle.

In some embodiments, the first connector assembly includes a support member mounted to the first housing. In some embodiments, the first electrical contacts are mounted to the support member.

In some embodiments, the first housing has a first housing receptacle. In some embodiments, the first electrical contacts include male electrical contacts that extend in the direction towards the distal end of the first housing within the first housing receptacle. In some embodiments, the second electrical contacts include female electrical contacts. The fluid resistant electrical connector can include electrical contact seals. Each of the electrical contact seals can be configured to interface with one of the first electrical contacts to block fluid ingress into a respective one of the second electrical contacts. The fluid resistant electrical connector can include a perimeter seal configured to interface with the second housing and a distal end of the first housing when the second connector assembly is connected with the first connector assembly to block fluid ingress into the first housing receptacle.

The fluid resistant electrical connector can include any suitable combination of the features described herein. For example, in some embodiments: (1) the fluid resistant electrical connector can include the support member, (2) the support member can have a flat plate configuration with apertures in which the coupling member and the first electrical contacts are mounted, (3) the first housing can have the first connector assembly receptacle, (4) the first electrical contacts can include male electrical contacts that extend within the first housing receptacle in the direction towards the distal end of the first housing, (5) the second electrical contacts can include female electrical contacts, (6) the fluid resistant electrical connector can include electrical contact seals, each of the electrical contact seals being configured to interface with one of the first electrical contacts to block fluid ingress into a respective one of the second electrical contacts; and/or (7) the fluid resistant electrical connector can include a perimeter seal configured to interface with the second housing and a distal end of the first housing when the second connector assembly is connected with the first connector assembly to block fluid ingress into the first housing receptacle.

In some embodiments, the retention member includes a shaped slot including a slot first portion and a slot second portion. In some embodiments, the slot first portion is configured to accommodate insertion of the distal portion of the coupling member into the slot first portion and the slot second portion is configured to retain the distal portion of the coupling member within the slot second portion.

The retention member can be shaped to prevent unintended movement of the retention member. For example, the retention member can be shaped to limit movement of the retention member relative to the second housing, when the slot first portion is aligned with the coupling member receptacle, to transverse movement towards alignment of the slot second portion with the coupling member receptacle. The retention member can be configured to be secured to the second housing to prevent movement of the retention member relative to the second housing that would move the slot second portion away from the distal portion of the coupling member. For example, the second housing can include an externally-exposed aperture oriented transverse to and intersecting the retention member receptacle and the retention member can include a retention aperture configured to align with the externally-exposed aperture of the second housing to accommodate a suture configured to secure the retention member to the second housing.

In some embodiments, the first electrical connectors include male electrical contacts. Any suitable number of male electrical contacts can be used. For example, in some embodiments, the first electrical contacts include three male electrical contacts.

The electrical connector can be used in any suitable implantable medical device. For example, in some embodiments the fluid resistant electrical connector is included in a mechanical circulatory assist system.

In another aspect, a method of connecting an electrical cable to an implantable medical device is provided. The method includes supporting, via a first housing of a first connector assembly, an elongated coupling member included in the first connector assembly to extend in a direction towards a distal end of the first housing. Male electrical contacts are supported via the first housing. The male electrical contacts are electrically connected to one of the electrical cable and the implantable medical device, arranged around the elongated coupling member, and oriented to extend in the direction towards the distal end of the first housing. Female electrical contacts are supported via a housing of a second connector assembly. Each of female electrical contacts are electrically connected to the other of the electrical cable and the implantable medical device and configured to couple with a respective one of the male electrical contacts when the first connector assembly is connected to the second connector assembly. A distal portion of the coupling member is accommodated in a coupling member receptacle of the second housing. A retention member of the second connector assembly is moved transverse to the direction towards the distal end of the first housing to retain the distal portion of the coupling member in the coupling member receptacle.

In some embodiments, the method further includes supporting the male electrical contacts via a support member mounted to the first housing. The support member can be constrained via the elongated coupling member to prevent separation of the male electrical contacts from the female electrical contacts.

In some embodiments, the method further includes blocking fluid ingress into the electrical contacts. For example, the method can include blocking fluid ingress into the female electrical contacts via electrical contact seals. Each of the electrical contact seals can be configured to interface with one of the male electrical contacts when the first connector assembly is connected to the second connector assembly. The method can include blocking fluid ingress via a perimeter seal configured to interface with the second housing and a distal end of the first housing when the first connector assembly is connected to the second connector assembly.

In some embodiments, the method further includes inserting the distal portion of the coupling member into a shaped slot in the retention member. In some embodiments of the method, moving the retention member transverse to the direction towards the distal end of the first housing repositions the coupling member from a first portion of the shaped slot sized to accommodate insertion of the distal portion of the coupling member into the shaped slot to a second portion of the shaped slot sized to retain the distal portion of the coupling member.

In some embodiments, the method further includes limiting movement of the retention member relative to the second housing, when the slot first portion is aligned with the coupling member receptacle, to movement towards alignment of the slot second portion with the coupling member receptacle. For example, the retention member can have a protrusion that contacts the second housing to limit movement of the retention member relative to the second housing.

In some embodiments, the method further includes securing the retention member to the second housing to prevent movement of the retention member relative to the second housing that would move the distal portion of the coupling member away from the slot second portion. For example, securing the retention member to the second housing can include suturing the retention member to the second housing via an aperture in the retention member and one or more apertures in the second housing.

The male electrical contacts can include any suitable number of electrical contacts that are distributed around the elongated coupling member. For example, in some embodiments, the male electrical contacts include three male electrical contacts distributed around the elongated coupling member.

For a fuller understanding of the nature and advantages of the present invention, reference should be made to the ensuing detailed description and accompanying drawings.

DETAILED DESCRIPTION

In the following description, various embodiments of the present invention will be described. For purposes of explanation, specific configurations and details are set forth in order to provide a thorough understanding of the embodiments. However, it will also be apparent to one skilled in the art that the present invention may be practiced without the specific details. Furthermore, well-known features may be omitted or simplified in order not to obscure the embodiment being described.

Figure 1:
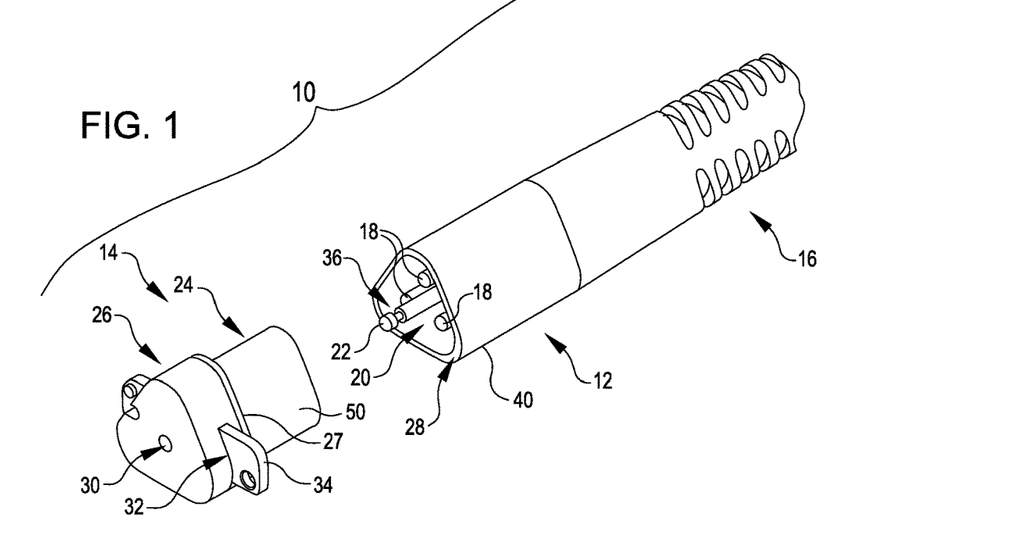
FIG. 1 shows a fluid resistant electrical connector suitable for use in an implantable medical device, in accordance with many embodiments.

Referring now to the drawings, in which like reference numerals represent like parts throughout the several views, FIG. 1 shows a fluid resistant electrical connector 10, in accordance with some embodiments. The fluid resistant electrical connector 10 includes a first connector assembly 12 and a second connector assembly 14. In the illustrated embodiment, the first connector assembly 12 is connected to an end of an electrical cable 16, the electrical cable 16 includes three conductors, and the first connector assembly 12 includes three male electrical contacts 18, each of which are connected to one of the three conductors of the electrical cable 16. In some embodiments, the second connector assembly 14 is integrated into an implantable medical device.

The second connector assembly 14 is configured to couple with the first electrical connector 12 to form a fluid tight electrical connection. The second connector assembly 14 includes three female electrical contacts (not visible in FIG. 1) that are configured to be connected with the male electrical contacts 18. The first connector assembly 12 includes a first housing 40 that forms a receptacle 20 through which the male electrical contacts 18 extend. The first connector assembly 12 includes an elongated coupling member 22 mounted to the first housing 40 and extending through the receptacle 20. The male electrical contacts 18 are arranged around the coupling member 22. The second connector assembly 14 includes a second housing 50 having a proximal portion 24 and a distal portion 26. The proximal portion 24 is shaped to be accommodated within the receptacle 20 when the second connector assembly 14 is coupled with the first connector assembly 12. In the illustrated embodiment, the three female contacts are mounted to the second housing 50 and accommodated within the proximal portion 24 of the second housing 50. The fluid resistant electrical connector 10 includes a perimeter seal 27 configured to extend around the proximal portion 24 of the second housing 50. In some embodiments the perimeter seal 27 is formed as an elastomeric seal. The perimeter seal 27 interfaces with a proximal surface of the distal portion 26 of the second housing 50 and a distal end surface 28 of the first housing 40 when the second connector assembly 14 is coupled with the first connector assembly 12 so as to inhibit fluid ingression into the receptacle 20.

The fluid resistant electrical connector 10 includes retention elements for preventing unintended decoupling of the first and second connector assemblies 12, 14. In the illustrated embodiment, the second connector assembly 14 includes a retention member 34 and the distal portion 26 of the second housing 50 includes a coupling member receptacle 30 and a retention member receptacle 32 configured to accommodate the retention member 34. The coupling member receptacle 30 is oriented and configured to receive a distal end portion of the elongated coupling member 22 so as to position a reduced diameter portion 36 of the coupling member 22 within a slot of the retention member 34. The retention member receptacle 32 is oriented transverse to the coupling member receptacle 30 and partially accommodates the retention member 34 and sliding of the retention member 34 between a first configuration in which the distal portion of the coupling member 22 can be inserted into the slot of the retention member 34 and a second configuration in which the distal portion of the coupling member 22 is retained within the slot of the retention member 34.

Figure 2:
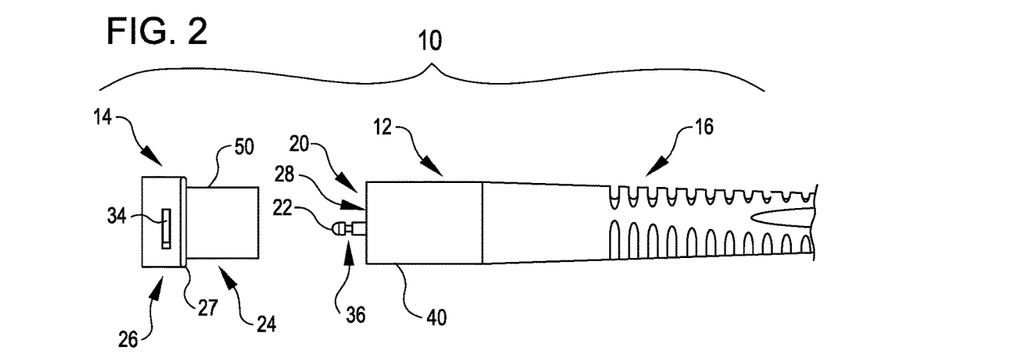
FIG. 2 shows a side view of the fluid resistant electrical connector of FIG. 1 in an uncoupled configuration.
Figure 3:
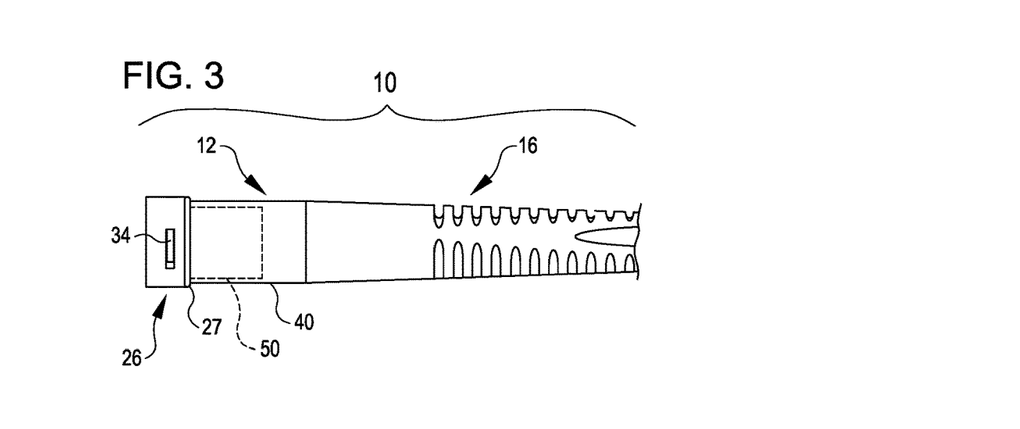
FIG. 3 shows a side view of the fluid resistant electrical connector of FIG. 1 in a coupled configuration.

FIG. 2 and FIG. 3 show a side view of the fluid resistant electrical connector 10 in an uncoupled configuration and a coupled configuration, respectively. As shown in FIG. 2, a distal portion of the coupling member 22 extends distally beyond the distal end surface 28 of the first housing 40 so that the reduced diameter portion 36 is disposed distal to the receptacle 20. As shown in FIG. 3, when the fluid resistant electrical connector 10 is in the coupled configuration, the proximal portion 24 of the second housing 50 is accommodated within the receptacle 20 and the perimeter seal 27 is interfaced with the distal portion 26 of the second housing 50 and the distal end surface 28 of the first housing 40, thereby blocking ingress of fluid into the receptacle 20. Although not shown in FIG. 3, the reduced diameter portion 36 of the coupling member 22 is positioned within a slot of the retention member 34 so that the retention member 34 can be slid to selectively retain the coupling member 22 via the retention member 34. The cooperation of retention member 34 and portion 36 prevents or reduces inadvertent decoupling of the first connector assembly 12 from the second connector assembly 14.

Figure 4:
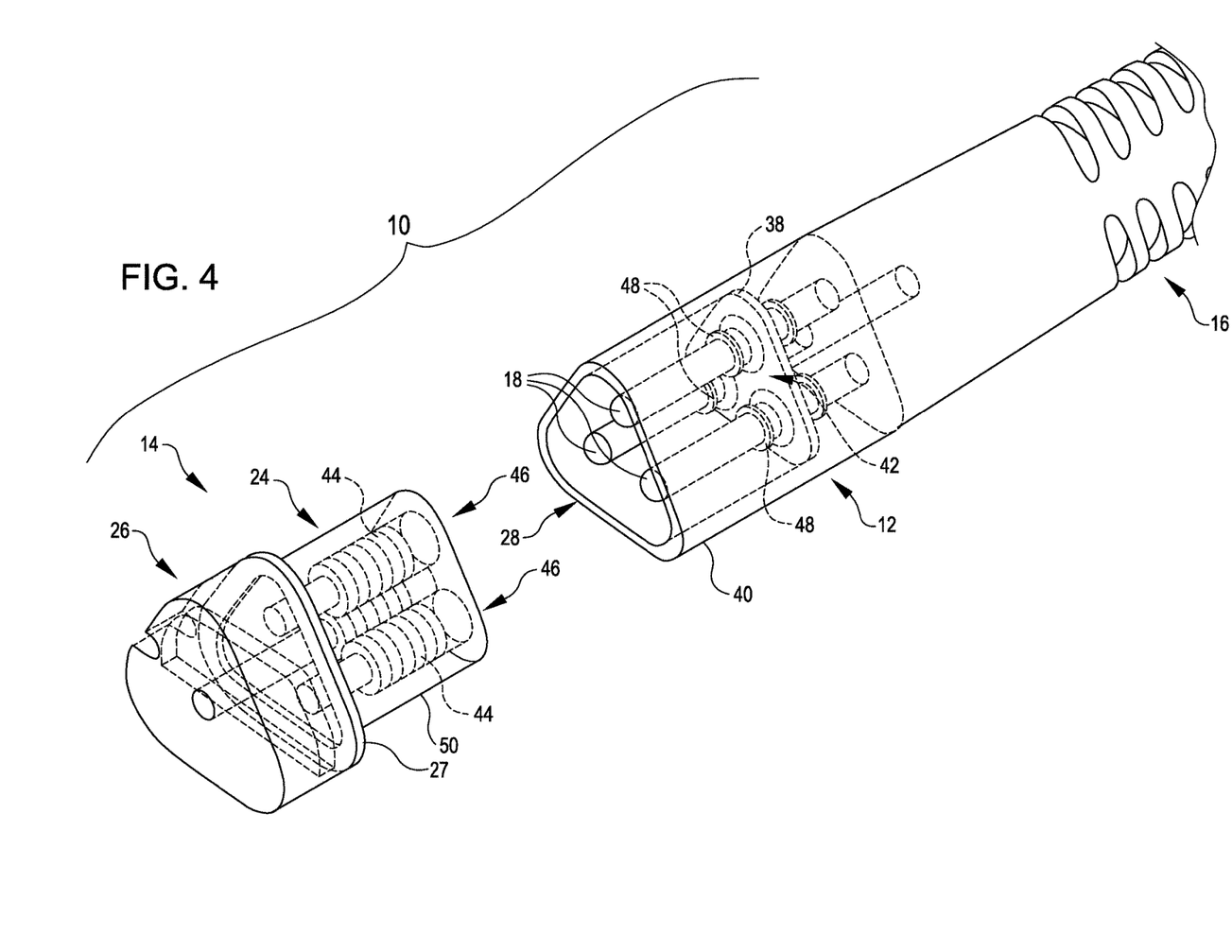
FIG. 4 shows the fluid resistant connector of FIG. 1 with portions of the connector partially transparent to show components that would otherwise be hidden from view.

FIG. 4 shows the fluid resistant electrical connector 10 with portions partially transparent so as to illustrate internal components. The first connector assembly 12 includes a support member 38 and the first housing 50. The second connector assembly 14 includes female electrical contacts 44 mounted within the proximal portion 24 of the second housing 50. In the illustrated embodiment, the support member 38 has a flat plate configuration and includes apertures through which each of the male electrical contacts 18 extend to connections with respective conductors in the electrical cable 16. Each of the male electrical contacts 18 are mounted to the support member 38. The support member 38 also includes a centrally-located aperture 42 through which a proximal portion of the coupling member 22 (not shown in FIG. 4) extends. The coupling member 22 is mounted to the support member 38. The male electrical contacts 18 are arranged in an array around the coupling member 22. When the first and second connector assemblies 12, 14 are coupled and the retention member 34 is positioned to retain the coupling member 22, the coupling member 22 restrains the position of the support member 38 relative to the retention member 34, thereby preventing inadvertent decoupling of the male electrical contacts 18 from the female electrical contacts 44.

The proximal portion 24 of the second housing 50 includes three apertures 46 in which the female electrical contacts 44 are mounted. The first connector assembly 12 includes three electrical contact seals 48, each of which extend around a base portion of a respective one of the male electrical contacts 18. Each of the electrical contact seals 48 is configured to block fluid ingress into a respective one of the apertures 46 when the electrical connector 10 is in the coupled configuration.

Figure 5:
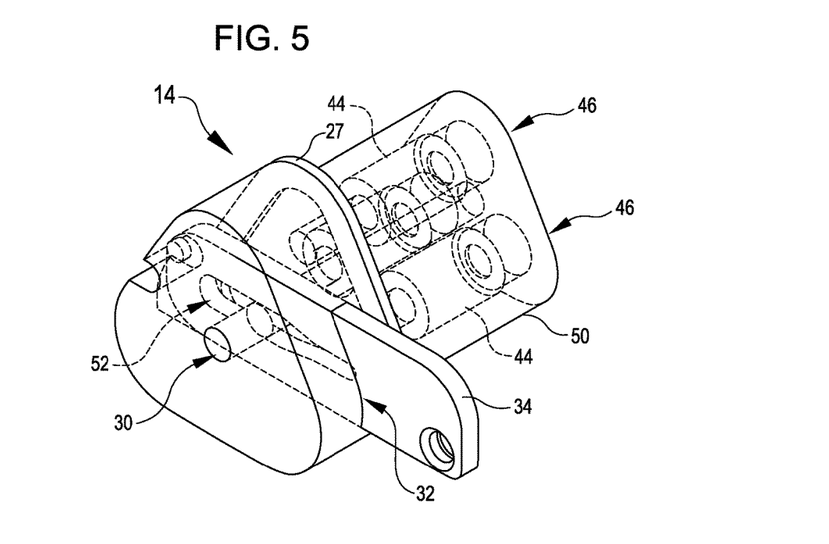
FIG. 5 illustrates details of a second connector assembly of the fluid resistant electrical connector of FIG. 1.

FIG. 5 shows the second connector assembly 14 with portions of the second housing 50 partially transparent so as to illustrate internal components. The second housing 50 includes the female contact apertures 46 in which the female electrical contacts 44 are disposed, the coupling member receptacle 30, and the retention member receptacle 32. The retention member receptacle 32 accommodates the retention member 34 and movement of the retention member 34 between an insertion configuration and a retention configuration. The retention member receptacle 32 intersects the coupling member receptacle 30. In the illustrated embodiment, the retention member 34 is movable in a direction perpendicular to the elongate direction of the coupling member 22. In alternate embodiments, the retention member can be movable in any suitable direction (e.g., substantially orthogonal) relative to the elongate direction of the coupling member 22. The retention member 34 includes a slot 52 through which a distal portion of the coupling member 22 is inserted to position the reduced diameter portion 36 for engagement with a narrow portion of the slot 52 to retain the coupling member 22 to prevent inadvertent decoupling of the electrical connector 10.

Figure 6:
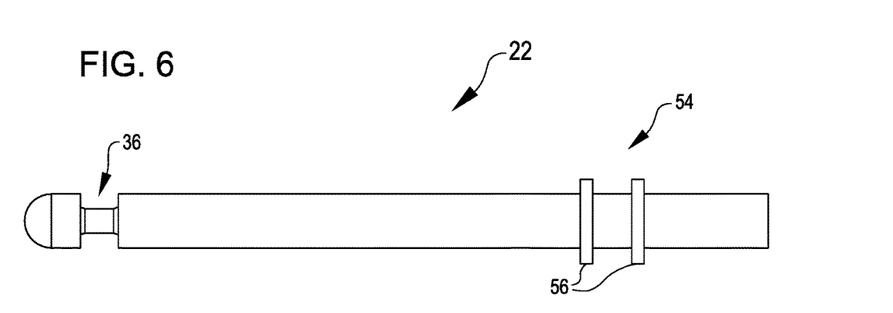
FIG. 6 shows a side view of an elongated coupling member of the fluid resistant electrical connector of FIG. 1.

FIG. 6 shows a side view of the elongated coupling member 22. The coupling member 22 includes a proximal portion 54 that includes mounting flanges 56 that interface with the support member 38 to block axial movement of the support member 38 relative to the coupling member 22, thereby constraining the position of the male electrical contacts 18 mounted to the support member 38 relative to the female electrical contacts 44 mounted in the second connector assembly 14. The mounting flanges 56 are spaced apart from the reduced diameter portion 36 so that the reduced diameter portion 36 is disposed within the slot 52 in the retention member 34 when the electrical connector 10 is in the coupled configuration. In many embodiments, the elongated coupling member 22 is made from a suitable material having suitable strength (e.g., a suitable metal such as a suitable stainless steel) and sized to react loading applied to the first and second connector assemblies 12, 14 that would disconnect the first and second connector assemblies 12, 14 but for the constraint applied to the first and second connector assemblies 12, 14 via the coupling member 22.

Figure 7:
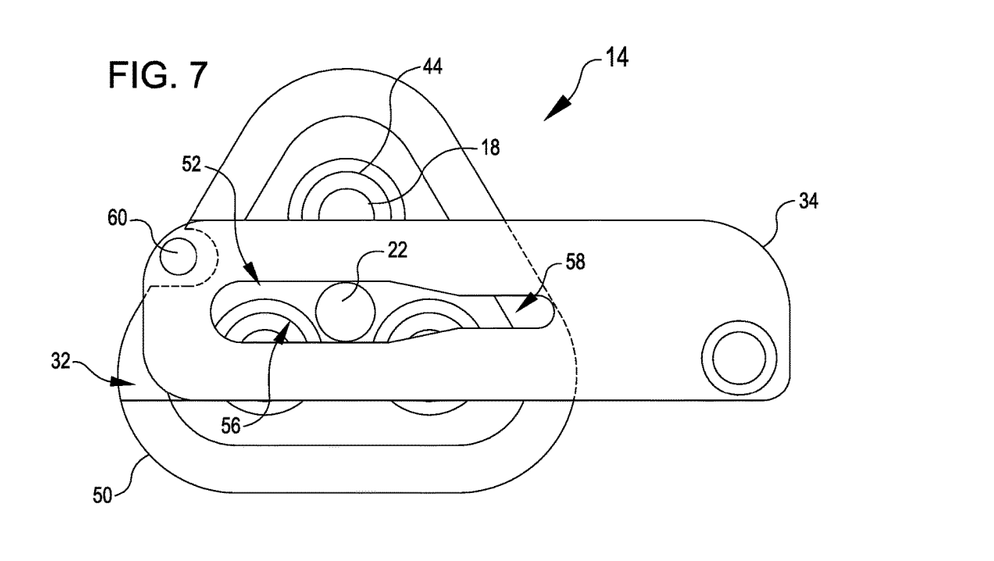
FIG. 7 shows a retention member of the fluid resistant electrical connector of FIG. 1 in an insertion configuration.

FIG. 7 shows the retention member 34 in an insertion configuration. The slot 52 in the retention member 34 includes a wide portion 56 and a narrow portion 58. The wide portion 56 is sized to accommodate insertion of the distal portion of the coupling member 22 through the slot 52 during coupling of the first and second connector assemblies 12, 14. The retention member 34 includes protrusions 60 that extend from the retention member 34 so as to interface with the second housing 50 to block sliding of the retention member 34 to the right in FIG. 7 to help prevent inadvertent removal of the retention member 34 from the retention member receptacle 32.

Figure 8:
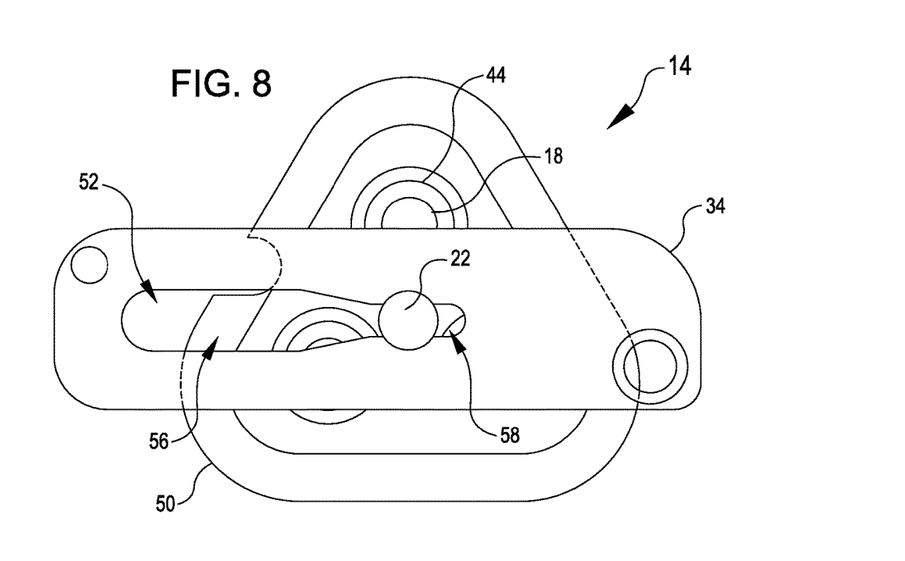
FIG. 8 shows the retention member of the fluid resistant electrical connector of FIG. 1 in a retention configuration.

FIG. 8 shows a retention member 34 in a retention configuration. In the retention configuration, the reduced diameter portion 36 is accommodated within the narrow portion 58 of the slot 52, thereby restraining movement of the coupling member 22 relative to the retention member 34 and the second housing 50. In the retention configuration shown, the restraint of the coupling member 22 prevents inadvertent decoupling of the electrical connector 10, thereby preventing inadvertent decoupling of the male electrical contacts 18 from the female electrical contacts 44.

Figure 9:
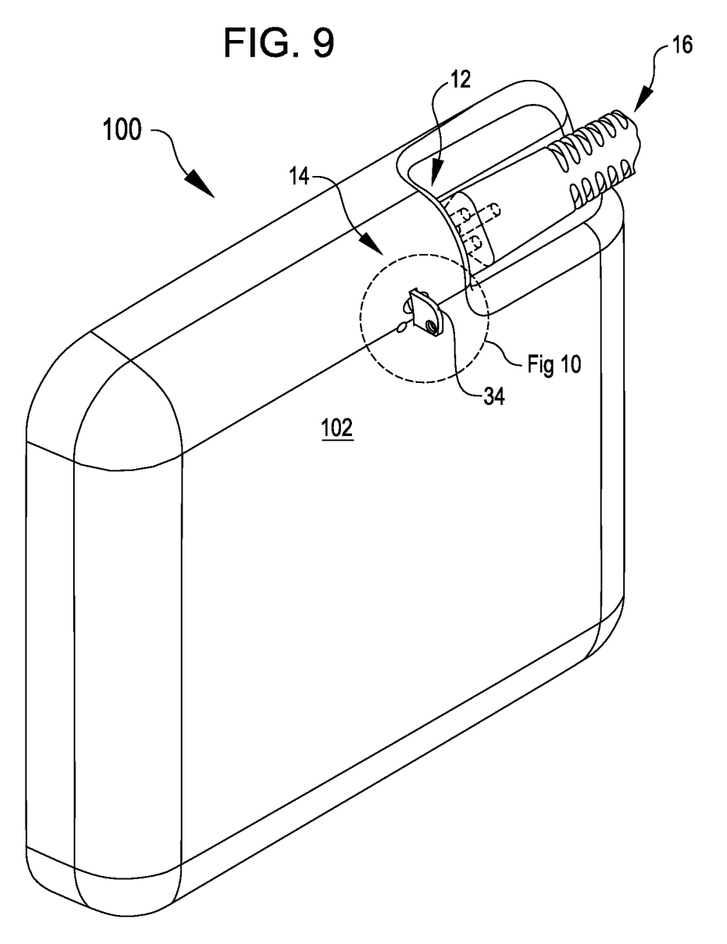
FIG. 9 shows an implantable medical device that includes the fluid resistant electrical connector of FIG. 1.

The fluid resistant electrical connector 10 can be included in any suitable implantable medical device system. For example, FIG. 9 shows an implantable medical device 100 that includes the fluid resistant electrical connector 10. In the illustrated embodiment, medical device 100 includes a housing 102 to which the second housing 50 is integrated. In the configuration shown in FIG. 9, the retention member 34 is in the insertion configuration, thereby accommodating coupling of the electrical cable 16 with the medical device 100 via the first and second connector assemblies 12, 14 of the fluid resistant electrical connector 10.

Figure 10:
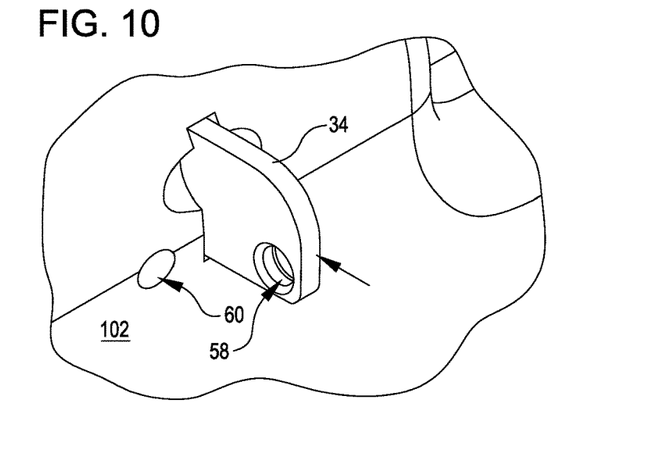
FIG. 10 shows a close-up of the implantable medical device of FIG. 9 illustrating the retention member in an insertion configuration.
Figure 11:
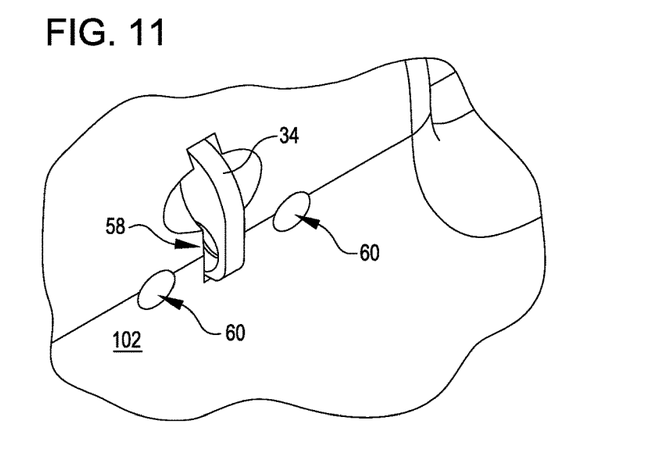
FIG. 11 shows a close-up of the implantable medical device of FIG. 9 illustrating the retention member in a retention configuration.
Figure 12:
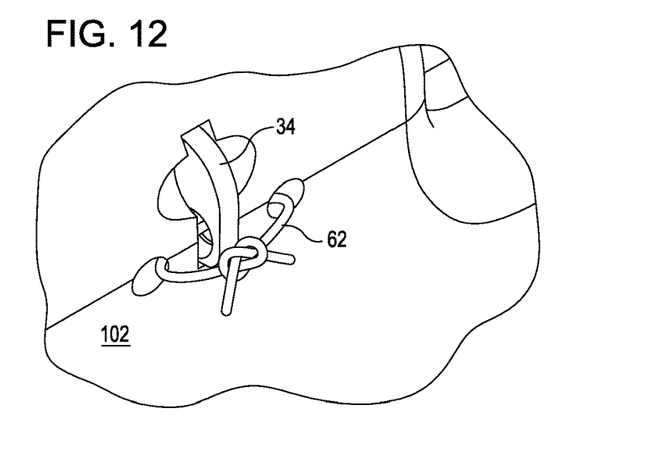
FIG. 12 shows a close-up of the implantable medical device of FIG. 9 illustrating the retention member secured in the retention configuration via a suture.
Figure 13:
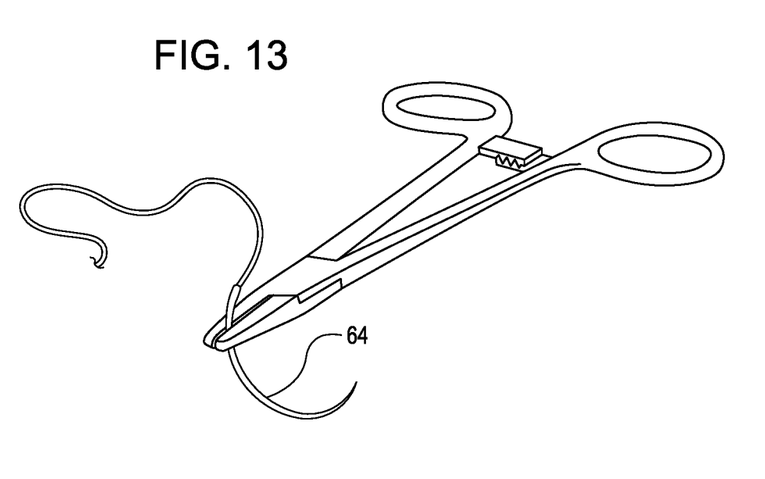
FIG. 13 shows a suture needle that can be used to secure the retention member via the suture.

FIG. 10 through FIG. 12 illustrate reconfiguration of the retention member from the insertion configuration to the retention configuration and to a secured configuration relative to the implantable medical device 100. From the insertion configuration shown in FIG. 10, the retention member 34 is pushed towards the housing 102 to reconfigure the retention member 34 to the retention configuration shown in FIG. 11. The retention member 34 includes a suture aperture 58 configured to align with suture apertures 60 in the housing 102 when the retention member 34 is in the retention configuration. FIG. 12 shows a close-up of the implantable medical device 100 illustrating the retention member 34 secured in the retention configuration via a suture 62. FIG. 13 shows a suture needle 64 that can be used to secure the retention member 34 via the suture 62. In some embodiments, the suture apertures 58, 60 are configured to accommodate a standard suture needle 64.

Other variations are within the spirit of the present invention. Thus, while the invention is susceptible to various modifications and alternative constructions, certain illustrated embodiments thereof are shown in the drawings and have been described above in detail. It should be understood, however, that there is no intention to limit the invention to the specific form or forms disclosed, but on the contrary, the intention is to cover all modifications, alternative constructions, and equivalents falling within the spirit and scope of the invention, as defined in the appended claims.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. The term "connected" is to be construed as partly or wholly contained within, attached to, or joined together, even if there is something intervening. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate embodiments of the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

All references, including publications, patent applications, and patents, cited herein are hereby incorporated by reference to the same extent as if each reference were individually and specifically indicated to be incorporated by reference and were set forth in its entirety herein.

What is claimed is:

1. A fluid resistant electrical connector for an implantable medical device, the electrical connector comprising:
    a first connector assembly comprising:
        a first housing having a first housing receptacle;
        a coupling member mounted to the first base housing and extending within the first housing receptacle in a direction towards a distal end of the first housing; and
        first electrical contacts mounted to the first housing, distributed around the coupling member, and extending within the first housing receptacle in the direction towards the distal end of the first housing;
    a second connector assembly connectable with the first connector assembly, the second connector assembly comprising:
        a second housing having a coupling member receptacle and a retention member receptacle, the coupling member receptacle being shaped to accommodate a distal portion of the coupling member, the retention member receptacle being oriented transverse to and intersecting the coupling member receptacle;
        second electrical contacts mounted to the second housing, each of the second electrical contacts being connected to a respective one of the first electrical contacts when the first connector assembly and the second connector assembly are connected; and
        a retention member at least partially accommodated by the retention member receptacle and moveable transverse to the direction towards the distal end of the first housing to retain the distal portion of the coupling member in the coupling member receptacle.

2. The electrical connector of claim 1, wherein:
    the first connector assembly comprises a support member mounted to the first housing; and
    the first electrical contacts are mounted to the support member.

3. The electrical connector of claim 1, wherein:
    the first electrical contacts comprise male electrical contacts that extend within the first housing receptacle in the direction towards the distal end of the first housing; and
    the second electrical contacts comprise female electrical contacts.

4. The electrical connector of claim 3, comprising electrical contact seals, each of the electrical contact seals interfacing with one of the first electrical contacts to block fluid ingress into a respective one of the second electrical contacts.

5. The electrical connector of claim 3, comprising a perimeter seal that interfaces with the second housing and a distal end of the first housing when the second connector assembly is connected with the first connector assembly to block fluid ingress into the first housing receptacle.

6. The electrical connector of claim 1, wherein the retention member has a shaped slot including a slot first portion and a slot second portion, the slot first portion accommodates insertion of the distal portion of the coupling member into the slot first portion, the slot second portion retains the distal portion of the coupling member within the slot second portion.

7. The electrical connector of claim 6, wherein the retention member is shaped to limit movement of the retention member relative to the second housing, when the slot first portion is aligned with the coupling member receptacle, to transverse movement towards alignment of the slot second portion with the coupling member receptacle.

8. The electrical connector of claim 6, wherein the retention member is securable to the second housing to prevent movement of the retention member relative to the second housing that would move the distal portion of the coupling member away from the slot second portion.

9. The electrical connector of claim 8, wherein:
    the second housing has an externally-exposed aperture transverse to and intersecting the retention member receptacle; and
    the retention member has a retention aperture that can be aligned with the externally-exposed aperture of the second housing to accommodate a suture that secures the retention member to the second housing.

10. The electrical connector of claim 1, wherein the first electrical contacts comprises three male electrical contacts.

11. A fluid resistant electrical connector for an implantable medical device, the electrical connector comprising:
    a first connector assembly comprising:
        a first housing having a first housing receptacle;

a coupling member mounted to the first base housing and extending in a direction towards a distal end of the first housing; and male electrical contacts mounted to the first housing, distributed around the coupling member, and extending within the first housing receptacle in the direction towards the distal end of the first housing;

a second connector assembly connectable with the first connector assembly, the second connector assembly comprising:

a second housing having a coupling member receptacle and a retention member receptacle, the coupling member receptacle being shaped to accommodate a distal portion of the coupling member, the retention member receptacle being oriented transverse to and intersecting the coupling member receptacle;

female electrical contacts mounted to the second housing, each of the female electrical contacts being connected to a respective one of the male electrical contacts when the first connector assembly and the second connector assembly are connected;

electrical contact seals, each of the electrical contact seals interfacing with one of the male electrical contacts to block fluid ingress into a respective one of the female electrical contacts; and a retention member at least partially accommodated by the retention member receptacle and moveable transverse to the direction towards the distal end of the first housing to retain the distal portion of the coupling member in the coupling member receptacle.

12. The electrical connector of claim 11, wherein:
the first connector assembly comprises a support member mounted to the first housing; and
the male electrical contacts are mounted to the support member.

13. The electrical connector of claim 11, comprising a perimeter seal that interfaces with the second housing and a distal end of the first housing when the second connector assembly is connected with the first connector assembly to block fluid ingress into the first housing receptacle.

14. The electrical connector of claim 11, wherein the retention member has a shaped slot including a slot first portion and a slot second portion, the slot first portion accommodates insertion of the distal portion of the coupling member into the slot first portion, the slot second portion retains the distal portion of the coupling member within the slot second portion.

15. The electrical connector of claim 14, wherein the retention member is shaped to limit movement of the retention member relative to the second housing, when the slot first portion is aligned with the coupling member receptacle, to transverse movement towards alignment of the slot second portion with the coupling member receptacle.

16. The electrical connector of claim 14, wherein the retention member is securable to the second housing to prevent movement of the retention member relative to the second housing that would move the distal portion of the coupling member away from the slot second portion.

17. The electrical connector of claim 16, wherein:
the second housing has an externally-exposed aperture transverse to and intersecting the retention member receptacle; and
the retention member has a retention aperture that can be aligned with the externally-exposed aperture of the second housing to accommodate a suture that secures the retention member to the second housing.

18. A fluid resistant electrical connector for an implantable medical device, the electrical connector comprising:
a first connector assembly comprising:
a first housing having a first housing receptacle;
a coupling member mounted to the first base housing and extending in a direction towards a distal end of the first housing; and
male electrical contacts mounted to the first housing, distributed around the coupling member, and extending within the first housing receptacle in the direction towards the distal end of the first housing;
a second connector assembly connectable with the first connector assembly, the second connector assembly comprising:
a second housing having a coupling member receptacle and a retention member receptacle, the coupling member receptacle being shaped to accommodate a distal portion of the coupling member, the retention member receptacle being oriented transverse to and intersecting the coupling member receptacle;
female electrical contacts mounted to the second housing, each of the female electrical contacts being connected to a respective one of the male electrical contacts when the first connector assembly and the second connector assembly are connected;
a perimeter seal that interfaces with the second housing and a distal end of the first housing when the second connector assembly is connected with the first connector assembly to block fluid ingress into the first housing receptacle; and
a retention member at least partially accommodated by the retention member receptacle and moveable transverse to the direction towards the distal end of the first housing to retain the distal portion of the coupling member in the coupling member receptacle.

19. The electrical connector of claim 18, wherein:
the first connector assembly comprises a support member mounted to the first housing; and
the male electrical contacts are mounted to the support member.

20. The electrical connector of claim 18, wherein the retention member has a shaped slot including a slot first portion and a slot second portion, the slot first portion accommodates insertion of the distal portion of the coupling member into the slot first portion, the slot second portion retains the distal portion of the coupling member within the slot second portion.

21. The electrical connector of claim 20, wherein the retention member is shaped to limit movement of the retention member relative to the second housing, when the slot first portion is aligned with the coupling member receptacle, to transverse movement towards alignment of the slot second portion with the coupling member receptacle.

22. The electrical connector of claim 20, wherein the retention member is securable to the second housing to prevent movement of the retention member relative to the second housing that would move the distal portion of the coupling member away from the slot second portion.

23. The electrical connector of claim 22, wherein:
the second housing has an externally-exposed aperture transverse to and intersecting the retention member receptacle; and
the retention member has a retention aperture that can be aligned with the externally-exposed aperture of the second housing to accommodate a suture that secures the retention member to the second housing.

\* \* \* \* \*